United States Patent [19]

Nakane et al.

[11] 4,456,617

[45] Jun. 26, 1984

[54] 7-OXABICYCLOHEPTANE SUBSTITUTED AMINO PROSTAGLANDIN ANALOGS AND THEIR USE IN INHIBITING PLATELET AGGREGATION AND BRONCHOCONSTRICTION

[75] Inventors: Masami Nakane, Hopewell; Martin F. Haslanger, Lambertville, both of N.J.

[73] Assignee: E. R. Squibb & Sons, Inc., Princeton, N.J.

[21] Appl. No.: 457,538

[22] Filed: Jan. 12, 1983

[51] Int. Cl.³ ............... A61K 31/34; C07D 307/00
[52] U.S. Cl. ............................ 424/285; 549/463
[58] Field of Search ................. 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0032292  6/1982  European Pat. Off. .
2039909  8/1980  United Kingdom .

Primary Examiner—Henry R. Jiles
Assistant Examiner—Bernard Dentz
Attorney, Agent, or Firm—Lawrence S. Levinson; Burton Rodney

[57] ABSTRACT

7-Oxabicycloheptane substituted amino prostaglandin analogs are provided having the structural formula

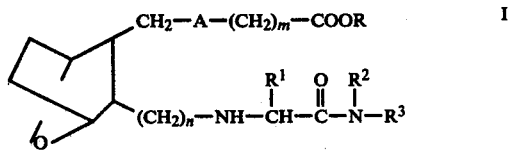

and including all stereoisomers thereof.

The compounds are cardiovascular agents useful, for example, in the treatment of thrombolytic disease.

13 Claims, No Drawings

7-OXABICYCLOHEPTANE SUBSTITUTED AMINO PROSTAGLANDIN ANALOGS AND THEIR USE IN INHIBITING PLATELET AGGREGATION AND BRONCHOCONSTRICTION

DESCRIPTION OF THE INVENTION

The present invention relates to 7-oxabicycloheptane substituted amino prostaglandin analogs which are cardiovascular agents useful, for example, in the treatment of thrombolytic disease. These compounds have the structural formula

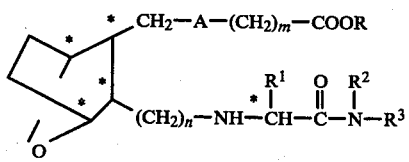

and including all stereoisomers thereof, wherein A is $CH=CH$ or $(CH_2)_2$; m is 1 to 8; n is 1 to 5; R is H or lower alkyl; $R^1$ is hydrogen, lower alkyl, aralkyl, hydroxyalkyl or aryl; and $R^2$ and $R^3$ may be the same or different and are hydrogen, lower alkyl, aryl, aralkyl, cycloalkyl, or cycloalkylalkyl, with the proviso that at least one of $R^2$ and $R^3$ is other than hydrogen.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl", "aryl-lower alkyl" or "cycloalkylalkyl" as used herein refers to lower alkyl groups as discussed above having an aryl substituent, such as benzyl, or a cycloalkyl substituent.

The term "halogen" or "halo" as used herein refers to chlorine, bromine, fluorine or iodine with chlorine being preferred.

The terms "$(CH_2)_m$" and "$(CH_2)_n$" includes a straight or branched chain radical having from 1 to 8 carbons in the normal chain in the case of "$(CH_2)_m$" and 1 to 5 carbons in the normal chain in the case of "$(CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

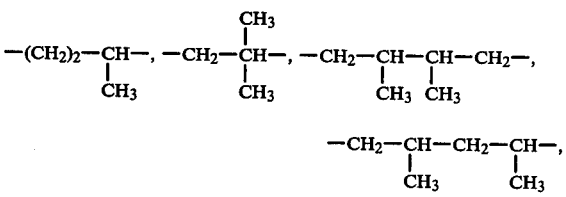

and the like.

Preferred are those compounds of formula I wherein A is $(CH_2)_2$ or $CH=CH$, m is 2 to 4, R is H, n is 1, and $R^1$ is hydrogen or lower alkyl, $R^2$ is hydrogen and $R^3$ is phenyl, benzyl or lower alkyl.

The various compounds of the invention may be prepared as outlined below.

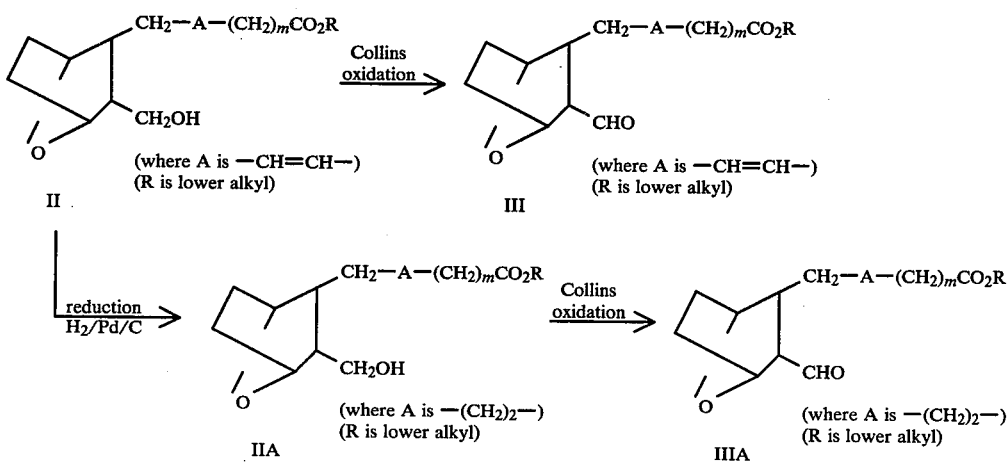

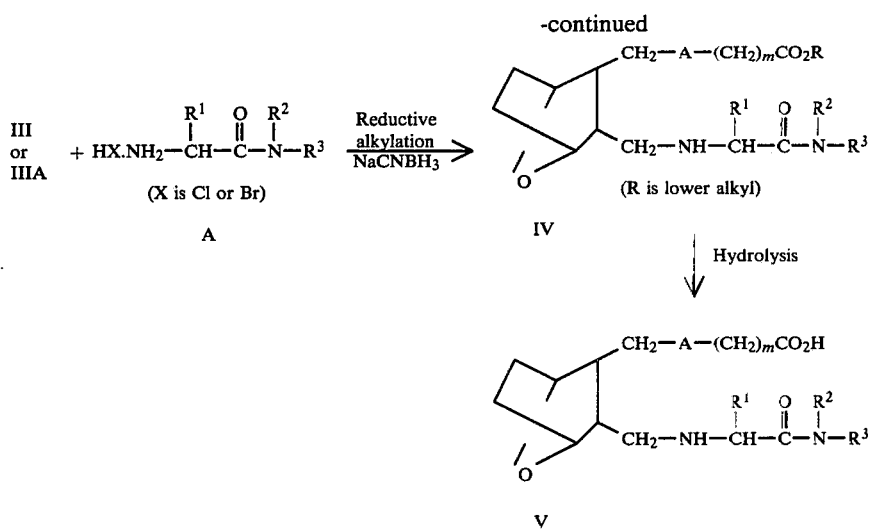

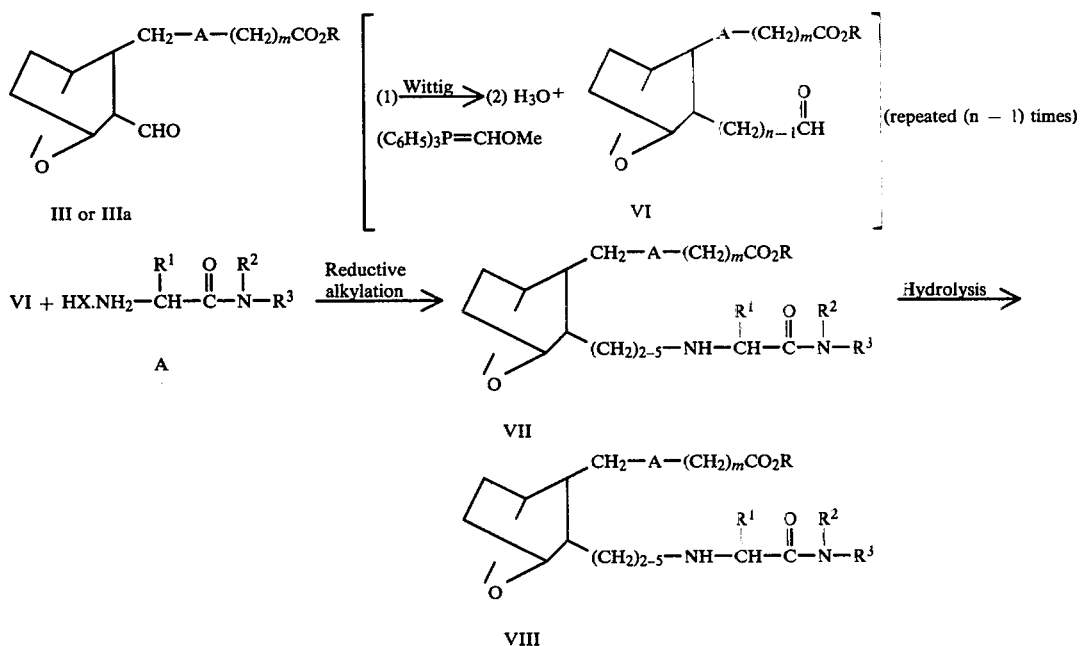

Where n is 2 to 5

In the reaction sequence identified as "A", the starting lower alkyl ester containing the hydroxymethyl group, that is, compound II, (prepared as described in U.S. Pat. No. 4,143,054) is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$), compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$).

As seen in reaction sequence "B", compounds of the invention where n is 1 that is

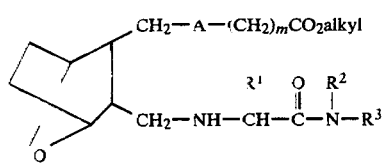

are prepared by reacting aldehyde III or IIIA with an amine of the structure

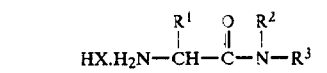

(wherein X is a halogen) employing a molar ratio of III or IIIA:amine A of within the range of from about 0.8:1 to about 1:1, in a solvent such as methanol or ethanol and a reducing agent such as sodium borohydride or sodium cyanoborohydride.

The reaction sequence identified as "C" is employed to prepare the compounds of the invention where n is 2 to 5, that is,

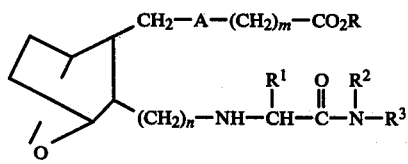  IA where n is 2 to 5

The aldehyde III or IIIA is used to prepare aldehyde VI (where n is 2–5) by carrying out a homologation sequence, such as a Wittig reaction with $(C_6H_5)_3P\!=\!CHOMe$ followed by hydrolysis, (n-1) times. The aldehyde VI (where n=2–5) is thus carried on to the compounds of this invention where n is 2–5, that is

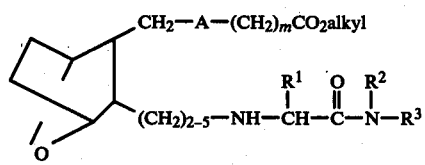  VII by reductive amination employing an amine of structure A in a weight ratio of VI:A of within the range of from about 0.8:1 to about 1:1 and a reducing agent such as sodium borohydride or sodium cyanoborohydride in a solvent such as methanol or ethanol and in the presence of acetic acid to form the compound of structure VII.

The esters IV and VII can be converted to the free acid, that is, to

IXA (A is —CH=CH—)
IXB (A is (CH$_2$)$_2$)

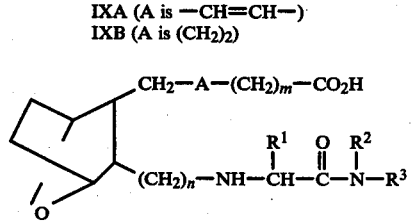

by treating the esters with a base, such as lithium hydroxide, followed by neutralization with an acid, such as dilute hydrochloric acid or oxalic acid.

The starting amine salt of structure A, that is $$HX.NH_2-CH(R^1)-C(=O)-N(R^2)-R^3$$  A may be prepared by reacting a solution of a protected amino acid of the structure B $$PRO-NH-CH(R^1)-COOH$$  B (wherein the amino protecting group PRO is t-butyloxycarbonyl, benzyloxycarbonyl, phthalyl, o-nitrophenylsulfenyl, tosyl and the like) in a solvent such as tetrahydrofuran with a condensing agent, such as carbonyldiimidazole and an amine of the structure C

to form the protected amine of the structure D $$Pro-NH-CH(R^1)-C(=O)-N(R^2)-R^3$$  D The protecting group (PRO) is removed from the formula D compound by reacting same with a strong acid such as trifluoroacetic acid, and hydrochloric acid or other appropriate reagent to form the amine salt A.

The compounds of this invention have four or five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

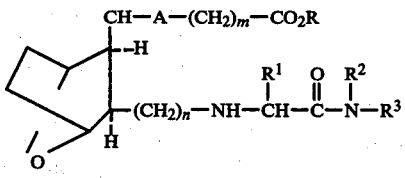  Ia (cis endo)

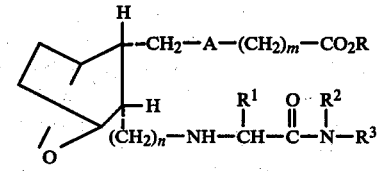  Ib (cis exo)

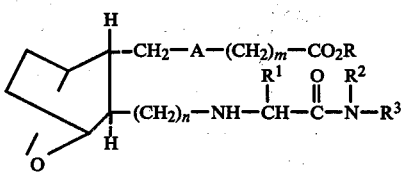

(trans)

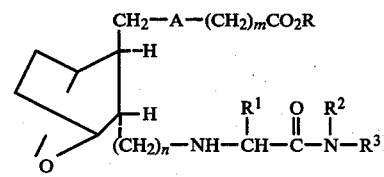

(trans)

The nucleus in each of the compounds of the invention is depicted as

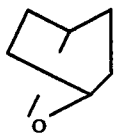

for matter of convenience; it will also be appreciated that the nucleus in the compounds of the invention may be depicted as

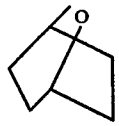

The compounds of this invention inhibit arachidonic acid-induced platelet aggregation and bronchoconstriction.

The compounds of this invention are cardiovascular agents useful as platelet aggregation inhibitors, e.g., for treatment of thrombolytic disease, such as coronary or cerebral thromboses. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of this invention.

EXAMPLE 1

[1β,2α(5Z),3α,4β]-7-[3-[[[2-Oxo-2-(phenylamino)-ethyl]-amino]methyl]-7-oxabicyclo[2.2.1]hept-2-yl]-5-heptenoic acid, methyl ester

A. Nα-(t-BOC)-Glycyl anilide

A solution of N-(t-butyloxycarbonyl)-glycine (4.38 g, 25 mmol) in dry THF (100 ml) was cooled to 0° C. in an argon atmosphere. Carbonyl diimidazole (CDI) (4.1 g, 25 mmol) was added and the mixture was stirred at 0° for 1 hours. Aniline (2.73 ml, 2.79 g, 30 mmol) was then added and the mixture was allowed to warm slowly to room temperature and left stirring overnight. The solvent was removed in vacuo. The residue was dissolved in $CH_2Cl_2$ (100 ml) and washed with 10% $KHSO_4$ solution (100 ml), saturated $NaHCO_3$ solution (100 ml) and $H_2O$ (100 ml). After drying ($MgSO_4$), the solvent was removed in vacuo leaving a tan solid (5.04 g, 81%). This sample was recrystallized from $EtOAc$-$Et_2O$ to give 3.5 g (56%) of the title A compound as a white crystalline material. TLC: silica gel, $Et_2O$, PMA and UV. $R_f=0.56$.

B. Glycyl anilide hydrochloride

The t-BOC derivative prepared in Part A (3.5 g, 14 mmol) was treated with cold (0°) distilled trifluoroacetic acid in an argon atmosphere. The solution was stirred at 0° C. for 50 minutes. The trifluoroacetic acid was removed in vacuo and benzene was added and removed in vacuo. The residue was dissolved in methanol and an excess of concentrated HCl solution was added. This solution was taken to dryness in vacuo. Twice ethanol was added and removed in vacuo leaving a solid which was triturated with $Et_2O$ and harvested by filtration to give the title B hydrochloride (2.61 g, 99%) as a white solid.

C.

[1β,2α(5Z),3α,4β]-7-[3-Formyl-7-oxabicyclo[2.2.1]hept-2-yl]-5-heptenoic acid, methyl ester A solution of pyridine (14.3 ml, 177 mmol) in dichloromethane (500 ml) was treated portionwise with chromium trioxide (8.9 g, 8.9 mmoles) with vigorous stirring. After addition was complete, the mixture was stirred at room temperature for 30 minutes, then treated with celite (30 g), then [1β,2α(5Z),3α,4β]-7-[3-(hydroxymethyl)-7-oxabicyclo-[2.2.1]hept-2-yl]-5-heptenoic acid, methyl ester prepared as described in U.S. Pat. No. 4,143,054 (4 g, 14.96 mmoles) in dichloromethane (20 ml) was added dropwise over a 20 minute period. The reaction mixture was stirred at room temperature for 30 minutes then filtered through celite. The filtrate was washed with 5% sodium bicarbonate (2×250 ml), 10% hydrochloric acid (2×100 ml) and again with 5% sodium bicarbonate (2×250 ml). The dichloromethane solution was dried overmagnesium sulfate, filtered and concentrated in vacuo. A brownish residue was dissolved in ether and passed through a pad of Baker silica gel, then eluted with more ether and the ether solution was taken to dryness in vacuo leaving 3.86 g of colorless oil.

D.

[1β,2α(5Z),3α,4β]-7-[3-[[[2-Oxo-2-(phenylamino)ethyl]amino]methyl]-7-oxabicyclo-[2.2.1]hept-2-yl]-5-heptenoic acid, methyl ester Part C aldehyde (532 mg, 2 mmol) was dissolved in methanol (20 ml) in an argon atmosphere. Sodium acetate (197 mg, 2.4 mmol) was added followed by the Part B hydrochloride (448 mg, 2.4 mmol) and $NaCNBH_3$ (126 mg, 2.0 mmol). After cooling in an ice bath, acetic acid (3.5 ml) was added dropwise. The cooling bath was removed and the mixture was stirred at room temperature 5 hours. 1N HCl solution was added to pH 1 and stirring was continued 45 minutes. A small amount of water was added and the mixture was basified with solid $NaHCO_3$. The product was extracted into ethyl acetate (3×50 ml). The combined extracts were washed with saturated NaCl solution (50 ml), dried ($MgSO_4$) and freed of solvent in vacuo leaving a viscous oil. This was chromatographed on silica gel (70 g) eluting with 2% MeOH in $CH_2Cl_2$ to give the title methyl ester as an oil (437.5 mg, 55%). TLC: 5% MeOH in $CH_2Cl_2$, vanillin; $R_f=0.33$.

EXAMPLE 2

[1β,2α(5Z),3α,4β]-7-[3-[[[2-Oxo-2-(phenylamino)-ethyl]amino]methyl]-7-oxabicyclo[2.2.1]hept-2-yl]-5-heptenoic acid The Example 1 methyl ester (313 mg, 0.78 mmol) was dissolved in THF (30 ml) and water (5 ml) in an argon atmosphere. 1N LiOH solution (7.8 ml) was added and the mixture was stirred at room temperature 5 hours.

After neutralizing with 1N HCl solution (7.8 ml), the solution was saturated with NaCl. The layers were separated and the aqueous was re-extracted with ethyl acetate (3×50 ml). The combined organic layers were dried (MgSO4) and freed of solvent in vacuo leaving 318.6 mg of viscous oil. This was chromatographed twice on SiliCAR CC-7 (25 g each time) eluting with 2-10% MeOH in CH2Cl2 to give 162 mg of material which solidified. This was triturated with Et2O, harvested by filtration and dried in vacuo at 80° to give the title acid product (128 mg, 42%). TLC: silica gel, 10% MeOH in CH2Cl2, vanillin; $R_f$=0.30.

Anal. Calcd for $C_{22}H_{30}O_4N_2 \cdot 0.25H_2O$: C, 67.58; H, 7.86; N, 7.16. Found: C, 67.50; H, 7.69; N, 6.97.

EXAMPLE 3

[1β,2α(5Z),3α,4β]-7-[3-[[[2-Oxo-2-(propylamino)ethyl]amino]methyl]-7-oxabicyclo[2.2.1]hept-2-yl]-5-heptenoic acid, methyl ester

A. Nα-(t-BOC)-Glycyl n-propylamide

A solution of t-BOC-glycine (8.75 g, 50 mmol) in dry THF (200 ml) was cooled to 0° in an argon atmosphere. CDI (8.1 g, 50 mmol) was added and the mixture was stirred at 0° for 1 hour. n-Propylamine (4.92 ml, 3.54 g, 60 mmol) was then added and the mixture was allowed to warm slowly to room temperature and left stirring overnight. The solvent was removed in vacuo. The residue was dissolved in CH2Cl2 (200 ml) and washed with 10% KHSO4 solution (200 ml), saturated NaHCO3 solution (200 ml) and water (200 ml). After drying (MgSO4), the solvent was removed in vacuo leaving 8.91 g (82.5%) of title A compound which was used without purification. TLC: silica gel, EtOAc, PMA; $R_f$=0.45.

B. Glycyl n-Propylamide hydrochloride

The title A t-BOC derivatives was treated with cold (0°) distilled trifluoroacetic acid (50 ml) in an argon atmosphere. The solution was stirred at 0° for 45 minutes. The solvent was removed in vacuo and toluene was added twice and removed in vacuo. The viscous residue was dissolved in methanol and an excess of concentrated HCl was added. This was taken to dryness in vacuo leaving a very viscous oil. This was further dried by twice adding methanol and removing in vacuo, then repeating twice with benzene and finally twice more with methanol. Trituration with ether gave the title B HCl salt as a hydroscopic solid (5.58 g, 90%).

C.
[1β,2α(5Z),3α,4β]-7-[3-[[[2-Oxo-2-(propylamino)ethyl]amino]methyl]-7-oxabicyclo-[2.2.1]hept-2-yl]-5-heptenoic acid, methyl ester

[1β,2α(5Z),3α,4β]-7-[3-Formyl-7-oxabicyclo-[2.2.1]hept-2-yl]-5-heptenoic acid, methyl ester (prepared as described in Example 1, Part C) (532 mg, 2 mmol) was dissolved in methanol (20 ml) in an argon atmosphere. Sodium acetate (246 mg, 3 mmol) was added followed by title B HCl salt (458 mg, 3 mmol) and NaCNBH3 (126 mg, 2 mmol). After cooling in an ice bath, HOAc (3.5 ml) was added dropwise. The cooling bath was removed and the mixture was stirred 3 hours at room temperature. 1N HCl solution was added to pH 1 and stirring was continued 45 minutes. A small amount of water was added and the mixture was basified with solid NaHCO3. The product was extracted into ethyl acetate (3×50 ml). The combined extracts were washed with NaCl solution (50 ml), dried (MgSO4) and freed of solvent in vacuo. The residue was chromatographed on silica gel 60 (70 g) eluting with 3% MeOH in CH2Cl2 to give title methyl ester compound as an oil (396 mg, 54%) TLC: silica gel, 10% MeOH in CH2Cl2, vanillin, $R_f$=0.48.

EXAMPLE 4

[1β,2α(5Z),3α,4β]-7-[3-[[[2-Oxo-2-(propylamino)ethyl]amino[methyl]-7-oxabicyalo[2.2.1]hept-2-yl]-5-heptenoic acid The Example 3 methyl ester (391 mg, 1.07 mg) was dissolved in THF (50 ml) and water (9 ml) in an argon atmosphere. 1N LiOH solution (10.7 ml) was added and the mixture was stirred at room temperature 3.5 hours. After adding 1N HCl solution (10.7 ml, pH~5) the mixture was poured into saturated NaCl solution (200 ml). This was extracted with EtOAc (3×100 ml). The combined extracts were washed with saturated NaCl solution, dried and freed of solvent in vacuo leaving only 44 mg. TLC indicated most of the product was in the aqueous layers. The combined aqueous layers were taken to near dryness in vacuo. Ethyl acetate (~400 ml) was added. The ethyl acetate solution was dried (MgSO4) filtered, freed of solvent in vacuo and combined with the sample from the first EtOAc extractions to give a total of 215.7 mg (57%) of crude product which failed to crystallize. This was chromatographed twice on SiliCAR CC-7 (15 g) eluting with 5-15% MeOH in CH2Cl2 to give material (178 mg) which was still somewhat contaminated with two slightly faster moving spots on TLC. This material was dissolved in a small amount of water and chromatographed on a HP20 column eluting with a water to acetonitrile gradient. The fractions containing only a trace of impurity were combined, freed of acetonitrile in vacuo and lyophilized to give title product (102.9 mg) as a white hygroscopic material.

Anal Calcd for $C_{19}H_{32}O_4N_2 \cdot 0.8L\ H_2O$: C, 62.16; H, 9.23; N, 7.63. Found: C, 62.16; H, 8.98; N, 7.62.

TLC: Silica gel, 15% MeOH in CH2Cl2, vanillin. $R_f$=0.16, trace at 0.22.

EXAMPLE 5

[1β,2α(5Z),3β,4β]-7-[3-[[[2-Oxo-2-(phenylamino)ethyl]amino]methyl]-7-oxabicyclo[2.2.1]hept-2-yl]-5-heptenoic acid, methyl ester

A. [1β,2α(5Z), 3β,4β]-7-[3-Formyl-7-oxabicyclo[2.2.1]hept-2-yl]-5-heptenoic acid, methyl ester A solution of pyridine (14.6 ml) in dichloromethane (500 ml) was treated portionwise with chromium trioxide (9.06 g) with vigorous stirring. After addition was complete, the mixture was stirred at room temperature for 30 minutes then treated with celite (30 g) then [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 (4.05 g, 15.1 mmoles) in dichloromethane (25 ml). The reaction mixture was stirred at room temperature for 30 minutes then filtered through celite. The filtrate was washed with 5% sodium bicarbonate (2×300 ml), 10% hydrochloric acid (2×300 ml) and again with 5% sodium bicarbonate (1×300 ml). The dichloromethane solution was dried over magnesium sulfate and concentrated in vacuo. The residue was dissolved in ether, and filtered through a pad of Baker silica gel, washed with ether and the filtrate taken to dryness in vacuo leaving 3.79 g (92%) of pale yellow oil.

B.

[1β,2α(5Z),3β,4β]-7-[3-[[[2-Oxo-2-(phenylamino)ethyl-]amino]methyl]-7-oxabicyclo[2.2.1]hept-2-yl]-5-heptenoic acid, methyl ester Part A aldehyde (532 mg, 2 mmol) is dissolved in methanol (20 ml) in an argon atmosphere. Sodium acetate (197 mg, 2.4 mmol) is added followed by the Example 1 Part B amine hydrochloride (448 mg, 2.4 mmol) and NaCNBH$_3$ (126 mg, 2.0 mmol). After cooling in an ice bath, acetic acid (3.5 ml) is added dropwise. The cooling bath is removed and the mixture is stirred at room temperature 5 hours. 1N HCl solution is added to pH 1 and stirring is continued 45 minutes. A small amount of water is added and the mixture is basified with solid NaHCO$_3$. The product is extracted into ethyl acetate (3×50 ml). The combined extracts are washed with saturated NaCl solution (50 ml), dried (MgSO$_4$) and freed of solvent in vacuo leaving a viscous oil. This is chromatographed on silica gel 60 (70 g) eluting with 2% MeOH in CH$_2$Cl$_2$ to give the title methyl ester as an oil.

EXAMPLE 6

[1β,2α(5Z),3β,4β]-7-[3-[[(2-Oxo-2-(phenylamino)ethyl-]amino]methyl]-7-oxabicyclo[2.2.1]hept-2-yl]-5-heptenoic acid The Example 5 methyl ester (304 mg, 0.82 mmol) is hydrolyzed in an argon atmosphere by dissolving in THF (25 ml) and water (6 ml) and treating with 1N LiOH solution (8.2 ml). After stirring at room temperature 6 hours, 1N HCl (8.2 ml) is added (pH~6) and the mixture is taken to near dryness in vacuo. The residue is dissolved in water and chromatographed on a HP-20 column eluting with a water to acetonitrile gradient to give material appearing clean by TLC (silica gel, 25% MeOH in CH$_2$Cl$_2$+trace NH$_4$OH, vanillin; R$_f$=0.18). These fractions are taken to near dryness in vacuo, dissolved in water and lyophilized to give the title product as a white fluffy amorphous material.

EXAMPLE 7

(1β,2β,3α,4β)-7-[3-[[[2-Oxo-2-(propylamino)ethyl]-amino]methyl]-7-oxabicyclo[2.2.1]hept-2-yl]heptanoic acid

A.

(1β,2β,3β,4β)-7-[3-(Hydroxymethyl)-7-oxabicyclo[2.2.1]hept-2-yl]heptanoic acid, methyl ester To 800 mg (3.0 mmole) of the [1β,2β(5Z),-3β,4β]-7-[3-(hydroxymethyl)-7-oxabicyclo[2.2.1]-hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1β,2β,3β,4β)-7-[3-Formyl-7-oxabicyclo[2.2.1]hept-2-yl]heptanoic acid, methyl ester To 1.21 g (5.6 mmole, 2.0 equiv.) of pyridinium chlorochromate (PCC) and 20 ml of anhydrous CH$_2$Cl$_2$ was added, under an argon atmosphere, 730 mg (2.8 mmole) of the title A alcohol in 2 ml of CH$_2$Cl$_2$. The reaction was stirred for 2 hours at 25°, diluted with 100 ml of ether, filtered through a pad of florisil, and evaporated to furnish 670 mg (88%) of the title B compound as a white crystalline solid.

C. (1β,2β,3α,4β)-7l-[3-Formyl-7-oxabicyclo-[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried over anhydrous magnesium sulfate ad concentrated to afford 765.0 mg (98%) of the title C aldehyde.

D.

(1β,2β,3α,4β)-7-[3-[[[2-Oxo-2-(propylamino)ethyl-]amino]methyl]-7-oxabicyclo-[2.2.1]hept-2-yl]heptanoic acid Following the procedure of Example 3, except substituting the Part C aldehyde for the Example 1A aldehyde, the title product is obtained.

EXAMPLE 8

[1β,2α(5Z),3β,4β]-7-[3-[[[2-Oxo-2-(propylamino)-ethyl]amino]methyl]-7-oxabicyclo[2.2.1]hept-2-yl]-5-heptenoic acid, methyl ester

[1β,2α(5Z),3β,4β]-7-[3-Formyl-7-oxabicyclo[2.2.1-]hept-2-yl]-5-heptenoic acid, methyl ester (prepared as described in Example 5 Part A) (532 mg, 2 mmol) is dissolved in methanol (20 ml) in an argon atmosphere. Sodium acetate (246 mg, 3 mmol) is added followed by Example 1 title B amine HCl salt (458 mg, 3 mmol) and NaCNBH$_3$ (126 mg, 2 mmol). After cooling in an ice bath, HOAc (3.5 ml) is added dropwise. The cooling bath is removed and the mixture is stirred 3 hours at room temperature. 1N HCl solution is added to pH 1 and stirring is continued 45 minutes. A small amount of water is added and the mixture is basified with solid NaHCO$_3$. The product is extracted into ethyl acetate (3×50 ml). The combined extracts are washed with NaCl solution (50 ml), dried (MgSO$_4$) and freed of solvent in vacuo. The residue is chromatographed on silica gel 60 (70 g) eluting with 3% MeOH in CH$_2$Cl$_2$ to give title methyl ester compound as an oil.

EXAMPLE 9

[1β,2α(5Z),3β,4β]-7-[3-[[[2-Oxo-2-(propylamino)ethyl]-amino]methyl]-7-oxabicyclo[2.2.1]hept-2-yl]-5-heptenoic acid The Example 8 methyl ester (391 mg, 1.07 mg) is dissolved in THF (50 ml) and water (9 ml) in an argon atmosphere. 1N LiOH solution (10.7 ml) is added and the mixture is stirred at room temperature 3.5 hours. After adding 1N HCl solution (10.7 mg, pH~5) the mixture is poured into saturated NaCl solution (200 ml). This is extracted with EtOAc (3×100 ml). The combined extracts are washed with saturated NaCl solution, dried and freed of solvent in vacuo leaving only 44 mg. TLC indicates most of the product is in the aqueous layers. The combined aqueous layers are taken to near dryness in vacuo. Ethyl acetate (~400 ml) is added. The ethyl acetate solution is dried (MgSO₄), filtered and freed of solvent in vacuo. This is chromatographed twice on SiliCAR CC-7 (15 g) eluting with 5–15% MeOH in CH₂Cl₂ to give material which is dissolved in a small amount of water and chromatographed on a HP20 column eluting with a water to acetonitrile gradient. The fractions containing only a trace of impurity are combined, freed of acetonitrile in vacuo and lyophilized to give title product as a white hygroscopic material.

EXAMPLE 10

[1β,2α(5Z),3α,4β]-7-[3-[[[2-Oxo-2-(phenylamino)-1-(methyl)ethyl]amino]methyl]-7-oxabicyclo[2.2.1]hept-2-yl]-5-heptenoic acid Following the procedure of Examples 1 and 2 except substituting t-BOC-alanine for the protected glycine, the title compound is obtained.

EXAMPLE 11

[1β,2α(5Z),3β,4β]-7-[3-[[[2-Oxo-2-(propylamino)-1-(s-butyl)ethyl]amino]methyl]-7-oxabicyclo[2.2.1]hept-2-yl]-5-heptenoic acid Following the procedure of Examples 3 and 4 except substituting t-BOC-leucine for the protected glycine, the title compound is obtained.

EXAMPLE 12

(1β,2β,3α,4β)-7-[3-[[[2-Oxo-2-(phenylamino)-1-(isopropyl)ethyl]amino]methyl]-7-oxabicyclo[2.2.1]-hept-2-yl]heptanoic acid Following the procedure of Example 7 except substituting t-BOC-valine for the protected glycine, the title compound is obtained.

EXAMPLE 13

[1β,2α(5Z),3α,4β]-7-[3-[[[2-Oxo-2-(propylamino)-1-(benzyl)ethyl]-amino]methyl]-7-oxabicyclo[2.2.1]hept-2-yl]-5-heptenoic acid Following the procedure of Examples 3 and 4 except substituting t-BOC-phenylalanine for the protected glycine, the title compound is obtained.

EXAMPLE 14

[1β,2α(5Z),3β,4β]-7-[3-[[[2-Oxo-2-(propylamino)-1-(hydroxymethyl)ethyl]amino]methyl]-7-oxabicyclo[2.2.1]-hept-5-yl]-5-heptenoic acid Following the procedure of Examples 8 and 9 except substituting t-BOC-serine for the protected glycine, the title compound is obtained.

EXAMPLE 15

(1β,2β,3α,4β)-7-[3-[[[2-Oxo-2-(benzylamino)ethylamino]methyl]-7-oxabicyclo[2.2.1]hept-2-yl]heptanoic acid Following the procedure of Example 7 except substituting benzylamine for n-propylamine, the title compound is obtained.

EXAMPLE 16

[1β,2α(5Z),3α,4β]-7-[3-[[[2-Oxo-2-(cyclohexylamino)ethyl]amino]methyl]-7-oxabicyclo[2.2.1]hept-2-yl]-5-heptenoic acid Following the procedure of Examples 1 and 2 except substituting cyclohexylamine for aniline, the title product is obtained.

EXAMPLE 17

[1β,2α(5Z),3β,4β]-7-[3-[[[2-Oxo-2-(cyclopentylamino)ethyl]amino]methyl]-7-oxabicyclo[2.2.1]hept-2-yl]-5-heptenoic acid Following the procedure of Examples 5 and 6 except substituting cyclopentylamine for aniline, the title product is obtained.

EXAMPLE 18

(1β,2α,3β,4β)-7-[3-[[[2-Oxo-2-(benzylamino)ethyl]amino]methyl]-7-oxabicyclo[2.2.1]hept-2-yl]heptanoic acid Following the procedure of Examples 7 and 3 except substituting benzylamine for aniline, the title product is obtained.

EXAMPLE 19

[1β,2α(5Z),3α,4β]-7-[3-[[[2-Oxo-2-2-[(ethyl)methylamino]ethyl]amino]methyl]-7-oxabicyclo[2.2.1]hept-2-yl]-5-heptenoic acid Following the procedure of Examples 1 and 2 except substituting ethylmethylamine for aniline, the title product is obtained.

EXAMPLE 20

[1β,2α(5Z),3α,4β]-7-[3-[[[2-Oxo-2-[(ethyl)phenylamino]ethyl]amino]methyl]-7-oxabicyclo[2.2.1]hept-2-yl]-5-heptenoic acid Following the procedure of Examples 1 and 2 except substituting (ethyl)phenylamine for aniline, the title product is obtained.

EXAMPLE 21

(1β,2α,3β,4β)-7-[3-[[[2-Hydroxy-2-oxo-2-[(cyclohexyl)methylamino]ethyl]amino]methyl]-7-oxabicyclo[2.2.1]hept-2-yl]heptanoic acid Following the procedure of Example 7 except substituting (cyclohexyl)methylamine for 2-propylamine, the title product is obtained.

EXAMPLE 22

[1β,2α(5Z),3α,4β]-7-[3-[[[2-Oxo-2-(phenylamino)ethyl]amino]ethyl]-7-oxabicyclo[2.2.1]hept-2-yl]-5-heptenoic acid

A.

[1β,2α(5Z),3α,4β]-7-[3-(2-Oxoethyl)-7-oxabicyclo[2.2.1]hept-2-yl]-5-heptenoic acid, methyl ester Into a dry 1000 ml round bottom 3-necked flask containing a stir bar was added dried 2.9 g (37.7 mmoles) methoxymethyltriphenylphosphonium chloride ($C_6H_5$)$_3P^+$—$CH_2OCH_3Cl^-$) and 235 ml distilled toluene (stored over molecular sieves). The resulting suspension was stirred in an ice bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated $NH_4Cl$ and extracted with ether (4×200 ml). The combined ether phases were washed with NaCl, saturated solution, and dried ($MgSO_4$) and concentrated to yield a yellow oil in a white crystalline solid (phosphine oxide). The white solid was triturated with EtOAc and purified by TLC on an LP-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl-7-oxabicyclo[2.2.1]hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1β,2α(5Z),3α,4β]-7-[3-[[[2-Oxo-2-(phenylamino)ethyl]amino]ethyl]-7-oxabicyclo[2.2.1]hept-2-yl]-5-heptenoic acid Following the procedure of Example 1 except substituting the part A aldehyde for the Example 1, Part C aldehyde, the title compound is obtained.

EXAMPLE 23

[1β,2α(5Z),3β,4β]-7-[3-[[[2-Oxo-2-(phenylamino)ethyl]amino]ethyl]-7-oxabicyclo[2.2.1]hept-2-yl]-5-heptenoic acid Following the procedure of Example 22, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 24

[1β,2β(5Z),3α,4β]-7-[3-[[[2-Oxo-2-(phenylamino)ethyl]-amino]ethyl]-7-oxabicyclo[2.2.1]hept-2-yl]heptenoic acid Following the procedure of Example 22 except substituting [1β,2β(5Z),3α,4β]-7-[3-formyl-7-oxabicyclo[2.2.1]hept-2-yl]-5-heptenoic acid, methyl ester for the [1β,2α(5Z),3α,4β]-7-[3-formyl-7-oxabicyclo[2.2.1]hept-2-yl]-5-heptenoic acid, methyl ester, the title compound is obtained.

EXAMPLE 25

[1β,2α(5Z),3α,4β]-7-[3-[[[2-Oxo-2-(phenylamino)-2-(methyl)ethyl]amino]ethyl]-7-oxabicyclo[2.2.1]hept-2-yl]-5-heptenoic acid Following the procedure of Example 22 except substituting t-BOC-alanine for the protected glycine, the title compound is obtained.

EXAMPLE 26

[1β,2α(5Z),3β,4β]-7-[3-[[[2-Oxo-2-(propylamino)-2-(s-butyl)ethyl]amino]ethyl]-7-oxabicyclo[2.2.1]hept-2-yl]-5-heptenoic acid Following the procedure of Example 23 except substituting t-BOC-leucine for the protected glycine, the title compound is obtained.

EXAMPLE 27

[1β,2β(5Z),3α,4β]-7-[3-[[[2-Oxo-2-(phenylamino)-2-(isopropyl)ethyl]amino]ethyl]-7-oxabicyclo[2.2.1]hept-2-yl]heptenoic acid Following the procedure of Example 24 except substituting t-BOC-valine for the protected glycine, the title compound is obtained.

EXAMPLE 28

[1β,2α(5Z),3α,4β]-7-[3-[[[2-Oxo-2-(propylamino)-2-(benzyl)ethyl]amino]ethyl]-7-oxabicyclo[2.2.1]hept-2-yl]-5-heptenoic acid Following the procedure of Example 22 except substituting t-BOC-phenylalanine for the protected glycine, the title compound is obtained.

EXAMPLE 29

[1β,2α(5Z),3β,4β]-7-[3-[[[2-Oxo-2-(propylamino)-2-(hydroxymethyl)ethyl]amino]ethyl]-7-oxabicyclo[2.2.1]hept-2-yl]-5-heptenoic acid Following the procedure of Example 23 except substituting t-BOC-serine for the protected glycine, the title compound is obtained.

EXAMPLE 30

[1β,2β(5Z),3α,4β]-7-[3-[[[2-Oxo-2-(benzylamino)ethyl]amino]ethyl]-7-oxabicyclo[2.2.1]hept-2-yl]heptenoic acid Following the procedure of Example 24 except substituting benzylamine for n-propylamine, the title compound is obtained.

EXAMPLE 31

[1β,2α(5Z),3α,4β]-7-[3-[[[2-Oxo-2-(cyclohexylamino)ethyl]amino]ethyl]-7-oxabicyclo[2.2.1]hept-2-yl]-5-heptenoic acid Following the procedure of Example 22 except substituting the cyclohexylamine for aniline, the title product is obtained.

EXAMPLE 32

[1β,2α(5Z),3β,4β]-7-[3-[[[2-Oxo-2-(cyclopentylethylamino)ethyl]amino]ethyl]-7-oxabicyclo[2.2.1]hept-2-yl]-5-heptenoic acid Following the procedure of Example 23 except substituting cyclopentylethylamine for aniline, the title product is obtained.

EXAMPLE 33

[1β,2α(5Z),3β,4β]-7-[3-[[[2-Oxo-2-(benzylamino)ethyl]amino]ethyl]-7-oxabicyclo[2.2.1]hept-2-yl]heptenoic acid Following the procedure of Example 24 except substituting benzylamine for aniline, the title product is obtained.

EXAMPLE 34

[1β,2α(5Z),3α,4β]-7-[3-[[[2-Oxo-[(ethyl)methylamino]ethyl]amino]ethyl]-7-oxabicyclo[2.2.1]hept-2-yl]-5-heptenoic acid Following the procedure of Example 22 except substituting (ethyl)methylamine for aniline, the title product is obtained.

EXAMPLE 35

[1β,2α(5Z),3α,4β]-7-[3-[[[2-Oxo-2-[(ethyl)phenylamino]ethyl]amino]ethyl]-7-oxabicyclo[2.2.1]hept-2-yl]-5-heptenoic acid Following the procedure of Example 22 except substituting (ethyl)phenylamine for aniline, the title product is obtained.

EXAMPLE 36

[1β,2α(5Z),3β,4β]-7-[3-[[[2-Hydroxy-2-oxo-2-[(cyclohexyl)methylamino]ethyl]amino]ethyl]-7-oxabicyclo[2.2.1]hept-2-yl]heptenoic acid Following the procedure of Example 24 except substituting (cyclohexyl)methylamine for 2-propylamine, the title product is obtained.

EXAMPLE 37

[1β,2α(5Z),3α,4β]-7-[3-[[[2-Oxo-(phenylamino)ethyl]amino]butyl]-7-oxabicyclo[2.2.1]hept-2-yl]-5-heptenoic acid A.
[1β,2α(5Z),3α,4β]-7-[3-(4-Oxo)butyl-7-oxabicyclo[2.2.1]hept-2-yl]-5-heptenoic acid, methyl ester

[1β,2α(5Z),3α,4β]-7-[3-(2-Oxoethyl)-7-oxabicyclo[2.2.1]hept-2-yl]-5-heptenoic acid, methyl ester is treated with methoxymethyltriphenylphosphonium chloride and potassium t-amylate employing the procedure described in Example 22. The product of this reaction is treated with aqueous trifluoroacetic acid to give [1β,2α(5Z),3α,4β]-7-[3-(3-oxo)propyl-7-oxabicyclo[2.2.1]hept-2-yl]-5-heptenoic acid, methyl ester. The compound is treated with methoxymethyltriphenylphosphonium chloride and potassium t-amylate employing the procedure described in Example 22. The product of the latter reaction is treated with aqueous trifluoroacetic acid to give the title A compound.

B.
[1β,2α(5Z),3α,4β]-7-[3-[[[2-Oxo-2-(phenylamino)ethyl]amino]butyl]-7-oxabicyclo[2.2.1]hept-2-yl]-5-heptenoic acid Following the procedure of Example 1 except substituting the part A aldehyde for the Example 1 part C aldehyde, the title compound is obtained.

EXAMPLE 38

[1β,2α(5Z),3β,4β]-7-[3-[[[2-Oxo-2-(phenylamino)ethyl]amino]butyl]-7-oxabicyclo[2.2.1]hept-2-yl]-5-heptenoic acid Following the procedure of Example 37, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 39

[1β,2β(5Z),3α,4β]-7-[3-[[[2-Oxo-2-(phenylamino)ethyl]amino]butyl]-7-oxabicyclo[2.2.1]hept-2-yl]heptanoic acid Following the procedure of Example 22, except substituting [1β,2β(5Z),3α,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 40

[1β,2α(5Z),3α,4β]-7-[3-[[[2-Oxo-2-(phenylamino)-2-(methyl)ethyl]amino]butyl]-7-oxabicyclo[2.2.1]hept-2-yl]-5-heptenoic acid Following the procedure of Example 37 except substituting t-BOC-alanine for the protected glycine, the title compound is obtained.

EXAMPLE 41

[1β,2α(5Z),3β,4β]-7-[3-[[[2-Oxo-2-(propylamino)-2-(s-butyl)ethyl]amino]butyl]-7-oxabicyclo[2.2.1]hept-2-yl]-5-heptenoic acid Following the procedure of Example 38 except substituting t-BOC-leucine for the protected glycine, the title compound is obtained.

EXAMPLE 42

[1β,2β(5Z),3α,4β]-7-[3-[[[2-Oxo-2-(phenylamino)-2-(isopropyl)ethyl]amino]butyl]-7-oxabicyclo[2.2.1]hept-2-yl]heptenoic acid Following the procedure of Example 39 except substituting t-BOC-valine for the protected glycine, the title compound is obtained.

EXAMPLE 43

[1β,2α(5Z),3α,4β]-7-[3-[[[2-Oxo-2-(propylamino)-2-(benzyl)ethyl]amino]butyl]-7-oxabicyclo[2.2.1]hept-2-yl]-5-heptenoic acid Following the procedure of Example 37 except substituting t-BOC-phenylalanine for the protected glycine, the title compound is obtained.

EXAMPLE 44

[1β,2α(5Z),3β,4β]-7-[3-[[[2-Oxo-2-(propylamino)-2-(hydroxymethyl)ethyl]amino]butyl]-7-oxabicyclo[2.2.1]hept-2-yl]-5-heptenoic acid Following the procedure of Example 38 except substituting t-BOC-serine for the protected glycine, the title compound is obtained.

EXAMPLE 45

[1β,2β(5Z),3α,4β]-7-[3-[[[2-Oxo-2-(benzylamino)ethylamino]butyl]-7-oxabicyclo[2.2.1]hept-2-yl]heptenoic acid Following the procedure of Example 39 except substituting benzylamine for n-propylamine, the title compound is obtained.

EXAMPLE 46

[1β,2α(5Z),3α,4β]-7-[3-[[[2-Oxo-2-(cyclohexylamino)ethyl]amino]butyl]-7-oxabicyclo[2.2.1]hept-2-yl]-5-heptenoic acid Following the procedure of Example 37 except substituting cyclohexylamine for aniline, the title product is obtained.

EXAMPLE 47

[1β,2α(5Z),3β,4β]-7-[3-[[[2-Oxo-2-(cyclopentylethylamino)ethyl]amino]butyl]-7-oxabicyclo[2.2.1]hept-2-yl]-5-heptenoic acid Following the procedure of Example 39 except substituting cyclopentylethylamine for aniline, the title product is obtained.

EXAMPLE 48

[1β,2α(5Z),3β,4β]-7-[3-[[[2-Oxo-2-(benzylamino)ethyl]amino]butyl]-7-oxabicyclo[2.2.1]hept-2-yl]heptenoic acid Following the procedure of Example 40 except substituting benzylamine for aniline, the title product is obtained.

EXAMPLE 49

[1β,2α(5Z),3α,4β]-7-[3-[[[2-Oxo-2-[(ethyl)methylamino]ethyl]amino]ethyl]-7-oxabicyclo[2.2.1]hept-2-yl]-5-heptenoic acid Following the procedure of Example 37 except substituting (ethyl)methylamine for aniline, the title product is obtained.

EXAMPLE 50

[1β,2α(5Z),3α,4β]-7-[3-[[[2-Oxo-2-(cyclohexylamino)ethyl]amino]butyl]-7-oxabicyclo[2.2.1]hept-2-yl]-5-heptenoic acid Following the procedure of Example 37 except substituting cyclohexylamine for aniline, the title product is obtained.

EXAMPLE 51

[1β,2α(5Z),3β,4β]-7-[3-[[[2-Oxo-2-(cyclopentylethylamino)ethyl]amino]butyl]-7-oxabicyclo[2.2.1]hept-2-yl]-5-heptenoic acid Following the procedure of Example 38 except substituting cyclopentylethylamine for aniline, the title product is obtained.

EXAMPLE 52

[1β,2α(5Z),3β,4β]-7-[3-[[[2-Oxo-2-(benzylamino)ethyl]amino]butyl]-7-oxabicyclo[2.2.1]hept-2-yl]heptenoic acid Following the procedure of Example 39 except substituting benzylamine for aniline, the title product is obtained.

EXAMPLE 53

[1β,2α(5Z),3α,4β]-7-[3-[[[2-Oxo-2-[(ethyl)methylamino]ethyl]amino]butyl]-7-oxabicyclo[2.2.1]hept-2-yl]-5-heptenoic acid Following the procedure of Example 37 except substituting (ethyl)methylamine for aniline, the title product is obtained.

EXAMPLE 54

[1β,2α(5Z),3α,4β]-7-[3-[[[2-Oxo-2-[(ethyl)phenylamino]ethyl]amino]butyl]-7-oxabicyclo[2.2.1]hept-2-yl]-5-heptenoic acid Following the procedure of Example 37 except substituting (ethyl)phenylamine for aniline, the title product is obtained.

EXAMPLE 55

[1β,2α(5Z),3β,4β]-7-[3-[[[2-Hydroxy-2-oxo-2-[(cyclohexyl)methylamino]ethyl]amino]butyl]-7-oxabicyclo[2.2.1]hept-2-yl]heptenoic acid Following the procedure of Example 39 except substituting (cyclohexyl)methylamine for 2-propylamine, the title product is obtained.

What is claimed is:

1. A compound having the structural formula

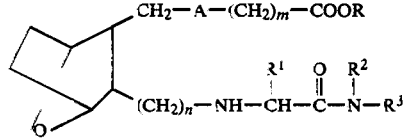

and including all stereoisomers thereof; wherein
A is —CH=CH— or —(CH₂)₂—;
m is 1 to 8; n is 1 to 5;
R is hydrogen or lower alkyl;
R¹ is hydrogen, lower alkyl, aralkyl, hydroxyalkyl or aryl;
R² and R³ are the same or different and are selected from the group consisting of hydrogen, lower alkyl, aryl, aralkyl, cycloalkyl and cycloalkylalkyl, with the proviso that at least one of R² and R³ is other than hydrogen; and wherein the term alkyl or lower alkyl by itself or as part of another group contains 1 to 12 carbons, the term aryl by itself or as part of another group is phenyl or naphthyl and which ring may be unsubstituted or substituted with a halogen, lower alkyl or lower alkoxy group, and the term cycloalkyl by itself or as part of another group contains 3 to 12 carbons and which may be unsubstituted or substituted with 1 or 2 halogens, 1 or 2 lower alkyl groups and/or lower alkoxy groups.

2. The compound as defined in claim 1 wherein R is H or CH₃.

3. The compound as defined in claim 1 wherein A is —CH=CH—.

4. The compound as defined in claim 1 wherein A is —CH=CH—, m is 2 to 4, n is 1, R is H or $CH_3$, $R^1$ is H, $R^2$ is H and $R^3$ is lower alkyl or aryl.

5. The compound as defined in claim 1 wherein A is —CH=CH—, m is 3, n is 1, R is H, $R^1$ is H, $R^2$ is H and $R^3$ is lower alkyl or phenyl.

6. The compound as defined in claim 1 having the name [1β,2α(5Z),3α,4β]-7-[[[2-oxo-2-(phenylamino)ethyl]amino]methyl]-7-oxabicyclo[2.2.1]hept-2-yl]-5-heptenoic acid or its methyl ester and including all stereoisomers thereof.

7. The compound as defined in claim 1 having the name [1β,2α(5Z),3α,4β]-7-[3-[[[2-oxo-2-(propylamino)ethyl]amino]methyl]-7-oxabicyclo[2.2.1]hept-2-yl]-5-heptenoic acid.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 1 to about 100 mg/kg.

10. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

11. A method of inhibiting platelet aggregation which comprises administering to a mammalian host an effective amount of a compound as defined in claim 1 or a pharmaceutically acceptable salt thereof.

12. A method of inhibiting bronchoconstriction associated with asthma, which comprises administering to a mammalian host an effective amount of a compound as defined in claim 1 or a pharmaceutically acceptable salt thereof.

13. A method of treating peripheral vascular diseases, which comprises topically or systemically administering to a mammalian host an effective amount of a compound as defined in claim 1 or a pharmaceutically acceptable salt thereof.

* * * * *